(12) United States Patent
Plowiecki

(10) Patent No.: US 7,722,597 B2
(45) Date of Patent: May 25, 2010

(54) SAFETY CATHETER FOR INJECTING FLUID

(75) Inventor: Nicolas Plowiecki, Montmorency (FR)

(73) Assignee: Balt Extrusion, Montmorency (FR)

( * ) Notice: Subject to any disclaimer, the term of this patent is extended or adjusted under 35 U.S.C. 154(b) by 0 days.

(21) Appl. No.: 12/089,411

(22) PCT Filed: Sep. 20, 2006

(86) PCT No.: PCT/FR2006/002146
§ 371 (c)(1),
(2), (4) Date: Apr. 7, 2008

(87) PCT Pub. No.: WO2007/039678
PCT Pub. Date: Apr. 12, 2007

(65) Prior Publication Data
US 2008/0228173 A1   Sep. 18, 2008

(30) Foreign Application Priority Data
Oct. 5, 2005   (FR) .................................. 05 10154
Jan. 20, 2006  (FR) .................................. 06 00502

(51) Int. Cl.
*A61M 25/16*   (2006.01)
(52) U.S. Cl. ..................... 604/534; 604/533; 604/535
(58) Field of Classification Search ................ 604/523, 604/533–535, 103, 907; 606/195
See application file for complete search history.

(56) References Cited

U.S. PATENT DOCUMENTS

| | | | |
|---|---|---|---|
| 6,296,622 | B1 | 10/2001 | Kurz et al. |
| 6,346,091 | B1 * | 2/2002 | Jacobsen et al. ............... 604/57 |
| 6,743,251 | B1 | 6/2004 | Eder |
| 2002/0082499 | A1 | 6/2002 | Jacobsen et al. |
| 2002/0111646 | A1 * | 8/2002 | Gifford et al. ............... 606/195 |
| 2004/0186464 | A1 | 9/2004 | Mamayek et al. |
| 2004/0225279 | A1 | 11/2004 | Raymond |
| 2005/0228360 | A1 * | 10/2005 | Kelley ......................... 604/523 |
| 2005/0277862 | A1 | 12/2005 | Anand |

* cited by examiner

*Primary Examiner*—Kevin C Sirmons
*Assistant Examiner*—Maria E Doukas
(74) *Attorney, Agent, or Firm*—Young & Thompson

(57) ABSTRACT

A catheter includes a tubular body having a channel having its ends opening out respectively at the ends of the tubular body, injector element for injecting fluid into the channel, a tubular endpiece having a channel with ends opening out respectively at the ends of the tubular endpiece, and element for connecting the endpiece and the body together so that the end of the channel and the end of the channel are in alignment on an axis, the connection element being constituted essentially by a ring that partially covers the body and the endpiece, and being also arranged in such a manner that the connection can be broken by exerting a force couple of predetermined value respectively on the endpiece and on the body. The invention is applicable to safety catheters for performing endovascular treatments by injecting embolic fluid, for example for treating arteriovenous malfunctions.

15 Claims, 2 Drawing Sheets ly well known.

SAFETY CATHETER FOR INJECTING FLUID

FIELD OF THE INVENTION

The present invention relates to safety catheters for injecting fluid, in particular embolic fluid, for endovascular treatments, e.g. for treating arteriovenous malfunctions (MAVs).

BACKGROUND OF THE INVENTION

Such treatment consists in injecting an embolic liquid by means of a catheter, for the purpose of plugging the vessel(s) supplying the diseased zone.

Unfortunately, it is known that it sometimes happens that the embolic liquid covers the distal end of the catheter used for injecting it and holds it captive in such a manner that it is necessary to pull on the catheter in an attempt to dislodge it.

It will readily be understood that such a maneuver can present drawbacks. For example, the embolic liquid can be withdrawn together with the catheter so that it no longer performs its function, or else it can become deposited in an undesired location, which can cause numerous small arteries to rupture. Another drawback occurs when the traction force is not sufficient and cannot be increased without running the risk of leading to major arterial lesions. Under such circumstances, the only solution is to leave practically the entire catheter in place in the body of the patient.

Various systems have been developed for avoiding leaving the entire catheter in place, e.g. the systems described in the following documents: US 2004/225279; US 2002/16582; and U.S. Pat. No. 6,743,251. Those systems are constituted essentially by a main tube terminated at its distal end by an endpiece butt-joined to the main tube via a bead of material in the form of a spacer that presents a weak point so as to be easily destroyed by various means. That can give satisfaction, providing that when the catheter is inserted, the endpiece does not become detached from the main tube before reaching the location that has been determined for injecting the fluid.

SUMMARY OF THE INVENTION

Thus, an object of the present invention is to provide a safety catheter for injecting fluid, in particular embolic fluid, that at least mitigates to a great extent the potential drawbacks mentioned above of similar catheters in the prior art.

More precisely, the present invention provides a safety catheter for injecting fluid, in particular embolic fluid, the catheter comprising:

a tubular body defined between a proximal end and a distal end, said tubular body comprising a first channel opening out at its first and second ends respectively at the proximal and distal ends of the tubular body;

injector means suitable for injecting the fluid into the first channel via the first end of said first channel;

a tubular endpiece defined between first and second ends, said tubular endpiece having a second channel opening out via its first and second ends respectively at the first and second ends of the tubular endpiece; and means for making a connection between said tubular endpiece and said tubular body in such a manner that the second end of the first channel and the first end of the second channel are substantially in alignment on an axis, said connection means also being arranged in such a manner that by exerting a force couple of determined value respectively on the tubular body and on the tubular endpiece, said connection is broken so as to separate the tubular body and the tubular endpiece;

the catheter being characterized by the fact that the connection means comprise a ring covering the side face portions respectively of the tubular body and of the tubular endpiece respectively at the distal end of the tubular body and at the first end of the tubular endpiece.

BRIEF DESCRIPTION OF THE DRAWINGS

Other characteristics and advantages of the present invention appear from the following description given with reference to the accompanying drawings provided by way of non-limiting illustration, in which.

It is stated initially that in the figures the same references are used to designate the same elements regardless of the figure in which they appear and regardless of the way in which said elements are shown. Similarly, if elements are not specifically referenced in one of the figures, their references can readily be found by referring to another figure.

DETAILED DESCRIPTION OF THE INVENTION

Figure 1:
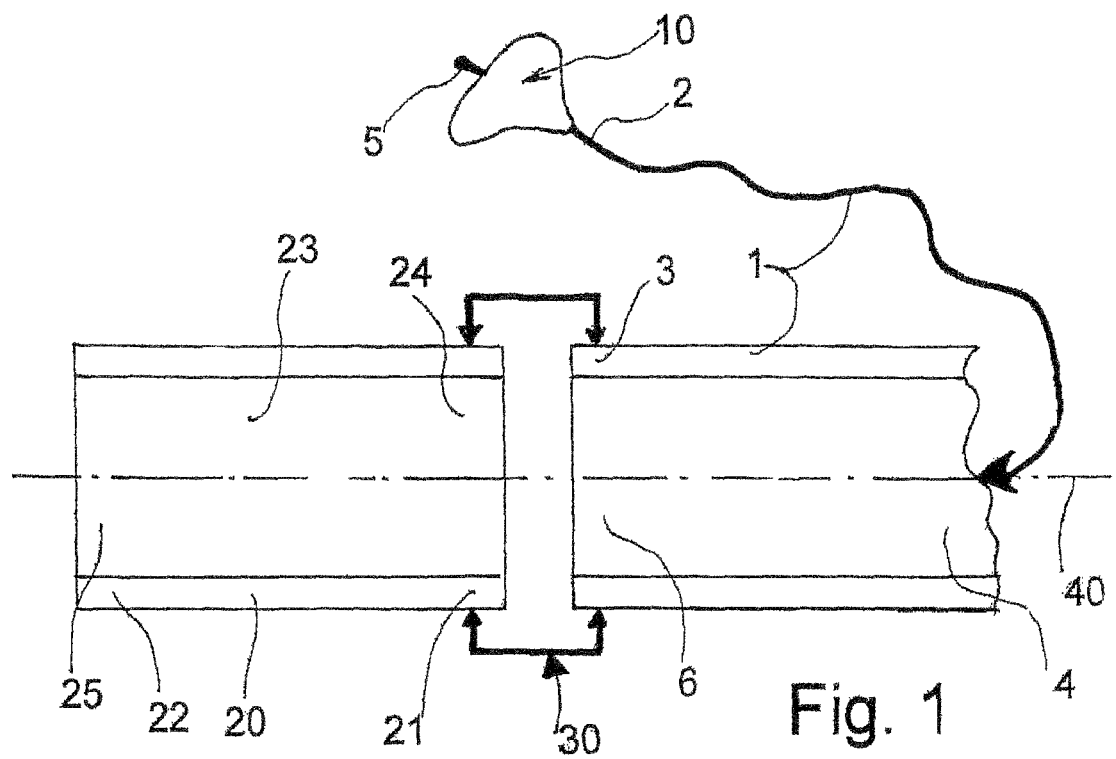
FIG. 1 is a skeleton diagram of a safety catheter of the invention for injecting fluid, in particular embolic fluid.

With reference to FIG. 1, the safety catheter for injecting fluid, in particular embolic fluid, comprises a tubular body 1 defined between a proximal end 2 and a distal end 3, the tubular body having a first channel 4 opening out at its first and second ends 5 and 6 respectively at the proximal and distal ends of the tubular body, and injector means 10 suitable for injecting the fluid into the first channel 4 via its first end 5.

The injector means 10 are themselves well known and are therefore not described in greater detail herein, solely for the purpose of simplifying the present description.

The catheter also includes a tubular endpiece 20 defined between first and second ends 21 and 22, the tubular endpiece having a second channel 23 that opens out via its first and second ends 24 and 25 respectively at the first and second ends 21 and 22 of the tubular endpiece 20, and means 30 for making a preferably-leaktight connection between the tubular body 1 and the tubular endpiece 20 so that the second end 6 of the first channel 4 and the first end 24 of the second channel 23 are substantially in alignment on an axis 40 so that the first and second channels 4, 23 form a substantially continuous channel, these connection means 30 also being arranged in such a manner that, by exerting a force couple of determined value respectively on the tubular body 1 and on the tubular endpiece 20, the connection is broken completely so as to separate the tubular body 1 from the tubular endpiece 20.

Figure 2:
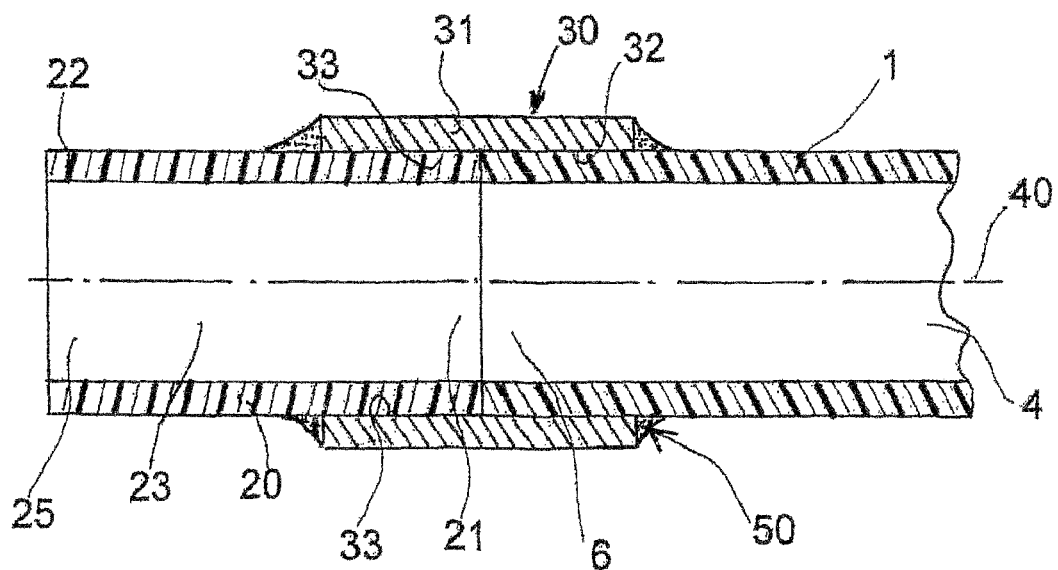
FIG. 2 is a fragmentary longitudinal section view of an embodiment of the safety catheter of the invention in compliance with the skeleton diagram shown in FIG. 1.

In a possible embodiment of the invention, as shown more particularly in FIG. 2 that should be taken in combination with what is shown in FIG. 1, the connection means 30 essentially comprise a sleeve-forming ring 31 covering the side faces 32, 33 respectively of the tubular body 1 and of the tubular endpiece 20 respectively at the distal end 3 of the tubular body and at the first end 21 of the tubular endpiece, and advantageously sealing means 50 for providing sealing between the ring 31 and the two side face portions 32 and 33.

Preferably, and regardless of the material used for making the tubular body 1 and the tubular endpiece 20, the ring 31 is made of platinum and the sealing means 50 are constituted by the adhesive binding the side wall of the ring with the two side face portions 32 and 33 respectively of the distal end 3 of the tubular body and of the first end 21 of the tubular endpiece.

By way of example, and as shown in FIG. 2, this adhesive is in the form of two beads providing a leaktight connection between each of the end edges of the ring 31 and the two respective side face portions 32 and 33 as defined above.

In general, the material from which the tubular body 1 and the endpiece 20 are made is, for example:
polyurethane, a polyamide, or a material known under the trademark "Pebax", or a mixture of these three materials.

In the diagram of FIG. 1, the tubular body 1 and the tubular endpiece 20 are shown relatively far apart from each other. However, as shown for example in FIG. 2, and for a purpose that is explained below, the tubular body and the tubular endpiece are advantageously in abutment.

The connection can be broken, as mentioned above, by applying a force couple of determined value respectively to the tubular endpiece 20 and to the tubular body 1. This force couple is constituted by at least one of the following couples: a force couple in traction, a twisting couple, or a combination of these two types of force couple.

The catheter of the invention as described above is used as follows.

When it is necessary to carry out an intervention as mentioned in the introduction to the present description, the catheter is inserted via the second end 22 of the endpiece 20 in the artery for treatment, starting from a point of the patient's body that is relatively accessible.

The tubular body 1 is pushed along until the second end of the endpiece reaches the place where treatment is to be performed, while its proximal end 5 with the injector means 10 is maintained outside the patient's body.

It should be emphasized, that while the tubular body is being pushed along, it pushes against the endpiece so that there is no risk of the connection between the body 1 and the endpiece 20 breaking, particularly since the endpiece is held securely both on the axis of the tubular body 1 and laterally by means of the ring 31.

The treatment liquid is then injected into the catheter at a determined pressure that, in order to enable the liquid to be ejected from the second end 25 of the second channel 23, is relatively higher than atmospheric pressure and/or the blood pressure that exists in an artery, and it delivers into the artery via said second end at the location in said artery that has been selected by the practitioner.

If, as mentioned above, the injected liquid forms a plug around the second end 22 of the tubular endpiece 20, which plug prevents the catheter from being withdrawn, the practitioner exerts a traction and/or twisting force on the proximal end of the tubular body 1. Under the action of this traction and/or twisting, because the connection means 30 have the above-defined characteristics, either the endpiece separates from the plug, or else the connection 30 breaks, i.e. the tubular endpiece 20 separates from the tubular body 1.

In the embodiment shown in FIG. 2, the connection means are generally arranged in such a manner that the bead of welding and/or adhesive connecting the ring 31 to the endpiece 20 is the first to break, thus making it possible to separate the endpiece and the assembly constituted by the ring and the tubular body.

The catheter of the invention, an embodiment of which is shown in FIG. 2, presents an important advantage. The ring 31 provides resistance to lateral deformation of the contacting ends of the tubular body 1 and of the tubular endpiece 20, where such deformation could be caused by the pressure of the injected fluid, but it does not oppose resistance to traction on the tubular body and therefore does not impede the endpiece 20 being separated from the body 1, as explained above.

Under no circumstances, is there any longer any need to leave nearly the entire catheter in place. At worst, only the endpiece is left in place in the patient's body, and it does present any danger.

Figure 3:
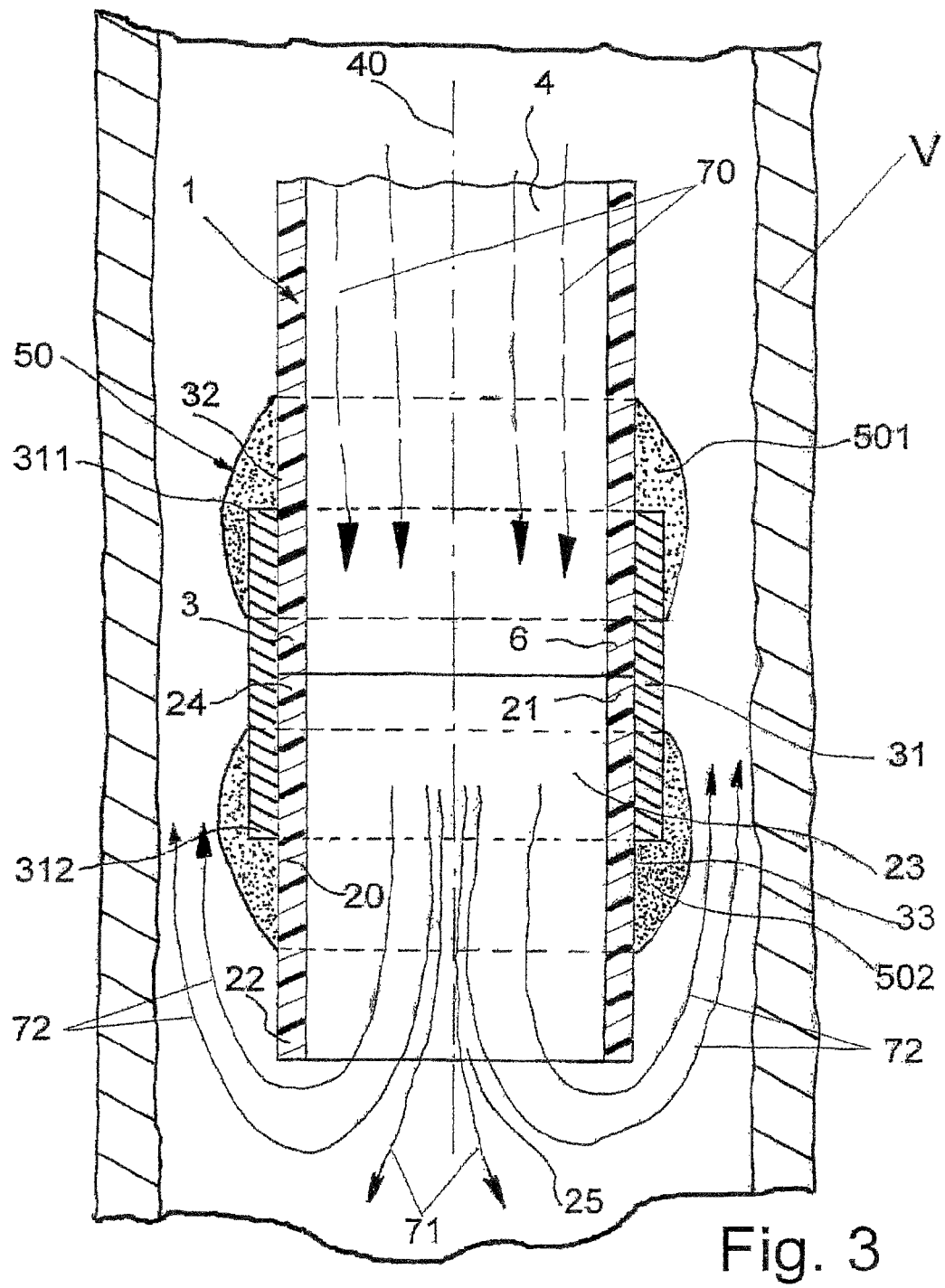
FIG. 3 shows an improvement of the embodiment of the catheter shown in FIG. 2.

FIG. 3 shows an improvement to the catheter embodiment described above.

The catheter in this improved embodiment has the same characteristics as those of the embodiment described with reference to FIG. 2, and in addition, at least a portion of the adhesive bonding the side wall of the ring 31 with the two side portions 32 and 33 respectively of the distal end 3 of the tubular body 1 and of the first end 21 of the tubular endpiece 20 presents the characteristic of being suitable for being destroyed by the fluid 70, specifically an endovascular treatment liquid, as mentioned above.

In an advantageous embodiment, the sealing means defined above are constituted by two beads of adhesive 501, 502 covering the two ends 311, 312 of the ring 31, at least in part if not completely, and covering respectively at least a fraction of the two side face portions 32, 33 preferably around their complete peripheries, respectively at the distal end 3 of the tubular body 1 and at the first end 21 of the tubular endpiece 20.

According to a characteristic of the invention, at least one of the two beads of adhesive 501, 502 is suitable for being destroyed by the fluid 70. Preferably, the bead of adhesive that is suitable for being destroyed by the fluid 70 is the bead 502 that is closer to the second end 22 of the tubular endpiece 20, the other bead 501 preferably not being destroyable by said fluid 70.

It should be understood that in the meaning of the present invention, the term "destroy" should be understood as having any one of the following effects: disintegration; decomposition; melting; breaking; dissolving; and regardless of whether this "destruction" is total or partial, such that it greatly diminishes the holding properties of the adhesive so that it can no longer perform its function of securing two parts one to the other.

The catheter of the embodiment shown in FIG. 3 and described above is used and functions as follows:

As described above, the tubular body 1 is pushed along until the second end 22 of the tubular endpiece 20 reaches the location to be treated, its proximal end 5 with the injector means 10 being maintained outside the patient's body.

The fluid 70, i.e. more particularly the treatment liquid, is then injected, and after it has traveled along the first and second channels 4 and 23, it flows out at 71 through the end 25 of the second channel 23. Nevertheless, a "plug" is formed very rapidly in front of this end, thereby, de facto, giving rise to reverse flow of the fluid 72 between the wall of the vein or the blood vessel V and the outside wall of the tubular endpiece 20.

Since the bead of adhesive 502 is designed to be dissolved by the fluid 70, it is eliminated, at least in part, and the ring 31 is suitable for being released from the tubular endpiece 20.

The structural characteristics of the adhesive as defined above make it possible, during injection of the fluid 70, initially to keep the tubular endpiece 20 and the tubular body 1 in abutment one against the other by means of the ring 31 that is adhesively bonded onto both of them, and subsequently, once the reverse flow 72 of the fluid occurs, to reduce progressively the bonding strength of the adhesive, while keeping the ring 31 still secured to the endpiece and the tubular body until the end of fluid injection, and finally, at the end of injection, to detach the ring 31 under relatively weak traction exerted on the tubular body.

The tubular body 1, the ring 31, and the bead of adhesive 501 can than be withdrawn, as explained above.

The Applicant has experimented with a catheter constituting this embodiment and has obtained very good results with the embolic fluid known under the trademark Onyx®, which fluid includes a solvent that enables the bonding strength of the adhesive to be decreased by at least 50% when the adhesive is based on polyurethane, which suffices to detach the tubular body 1 from the tubular endpiece 20 and to obtain the desired results.

The invention claimed is:

1. A safety catheter for injecting fluid, comprising:
a tubular body defined between a proximal end and a distal end, said tubular body comprising a first channel through the tubular body and opening out at the proximal end and at the distal end of the tubular body;
a tubular endpiece defined between a first end and a second end, said tubular endpiece comprising a second channel through the tubular endpiece and opening out at the first end and at the second end of the tubular endpiece; and
a connection means comprising a ring for making a connection between said tubular endpiece and said tubular body, and an adhesive for bonding the ring to at least one of the tubular body and the tubular endpiece,
wherein the tubular body and the tubular endpiece are connected in such a manner that the distal end of the first channel and the first end of the second channel are substantially in alignment on an axis, the ring covers an exterior side face of the distal end of the tubular body and an exterior side face of the first end of the tubular endpiece, the adhesive is disposed on the exterior surface of the ring to bond the ring to at least one of the distal end of the tubular body and the first end of the tubular endpiece, and said connection means is arranged in such a manner, that by exerting a force couple of determined value respectively on the tubular body and on the tubular endpiece, said connection is broken so as to separate the tubular body and the tubular endpiece.

2. The catheter according to claim 1, wherein the adhesive is disposed on a side wall of the ring and on at least one of i) an exterior side face of the tubular body and ii) an exterior side face the tubular endpiece.

3. The catheter according to claim 1, wherein the adhesive is capable of being destroyed by the fluid.

4. The catheter according to claim 1, wherein the adhesive seals the ring to both the tubular body and the tubular endpiece.

5. The catheter according to claim 2, wherein the connection means comprises two beads of adhesive, a first bead disposed on the exterior side face of the tubular body and a second bead disposed on the exterior side face of the tubular endpiece.

6. The catheter according to claim 5, wherein at least one of the two beads of adhesive is capable of being destroyed by the fluid.

7. The catheter according to claim 6, wherein the at least one of the two beads of adhesive that is capable of being destroyed by the fluid is the second bead that is disposed on the exterior side face of the tubular endpiece.

8. The catheter according to claim 2, wherein the adhesive is capable of being destroyed by being dissolved by the fluid.

9. The catheter according to claim 1, wherein the connection means makes it possible, during initial injection of the fluid, to keep the tubular body and the tubular endpiece in abutment one against the other by means of the ring adhesively bonded onto the tubular body and the tubular endpiece, and subsequently, once a reverse flow of the fluid occurs, to reduce progressively the bonding strength of the adhesive while keeping the ring still secured to the tubular body and the tubular endpiece until the end of fluid injection, and finally, at the end of fluid injection, to allow the ring to detach under traction exerted on the tubular body.

10. The catheter according to claim 5, wherein the connection means makes it possible, during initial injection of the fluid, to keep the tubular body and the tubular endpiece in abutment one against the other by means of the ring adhesively bonded onto the tubular body and the tubular endpiece, and subsequently, once a reverse flow of the fluid occurs, to reduce progressively the bonding strength of the adhesive while keeping the ring still secured to the tubular body and the tubular endpiece until the end of fluid injection, and finally, at the end of fluid injection, to allow the ring to detach under relatively weak traction exerted on the tubular body.

11. The catheter according to claim 1, wherein the tubular body and the tubular endpiece are connected in end-to-end abutment.

12. The catheter according to claim 1, wherein the force couple is at least one of traction force, twisting, and a combination of force couple thereof.

13. The catheter according to claim 1, wherein the connection between the tubular body and the tubular endpiece is leaktight.

14. The catheter according to claim 1, wherein the opening of the first channel at the distal end of the tubular body and the opening of the second channel at the first end of the tubular endpiece are substantially in alignment on an axis so that the first channel and the second channel form a continuous channel.

15. The catheter according to claim 1, further comprising an injector means for injecting the fluid into the first channel via the opening at the proximal end of the tubular body.

\* \* \* \* \*